United States Patent
Claereboudt et al.

(10) Patent No.: US 10,016,623 B2
(45) Date of Patent: Jul. 10, 2018

(54) PARTICLE THERAPY SYSTEM AND METHOD WITH PARALLEL CONTROL OF ENERGY VARIATION AND BEAM POSITION VARIATION

(71) Applicant: Ion Beam Applications, Louvain-la-Neuve (BE)

(72) Inventors: Yves Claereboudt, Louvain-la-Neuve (BE); Damien Prieels, Louvain-la-Neuve (BE)

(73) Assignee: Ion Beam Applications S.A., Louvain-la-Neuve (BE)

( * ) Notice: Subject to any disclaimer, the term of this patent is extended or adjusted under 35 U.S.C. 154(b) by 0 days.

(21) Appl. No.: 15/375,259

(22) Filed: Dec. 12, 2016

(65) Prior Publication Data
US 2017/0165502 A1    Jun. 15, 2017

(30) Foreign Application Priority Data
Dec. 11, 2015    (EP) .................................... 15199614

(51) Int. Cl.
*A61N 5/10*      (2006.01)
*G21K 5/04*      (2006.01)
*H05H 7/04*      (2006.01)
*H05H 13/00*     (2006.01)
(Continued)

(52) U.S. Cl.
CPC ........... *A61N 5/1043* (2013.01); *A61N 5/103* (2013.01); *A61N 5/107* (2013.01); *A61N 5/1081* (2013.01); *H05H 7/04* (2013.01); *A61N 2005/1076* (2013.01); *A61N 2005/1087* (2013.01); *H05H 13/005* (2013.01); *H05H 13/02* (2013.01);
(Continued)

(58) Field of Classification Search
CPC ........ A61N 5/10; A61N 5/103; A61N 5/1043; A61N 5/1048; A61N 5/1079; A61N 5/1077; A61N 5/1081; G21K 5/04; G21K 5/10; G21K 1/04; G21K 1/10; A61B 6/037; A61B 6/4258; A61B 6/583
USPC ............................................................. 600/1
See application file for complete search history.

(56) References Cited

U.S. PATENT DOCUMENTS 8,109,865 B2 * 2/2012 Jackson .................. A61N 5/10
                                                          600/1
9,185,789 B2 * 11/2015 Zwart ..................... H05H 13/02
9,630,021 B2 *  4/2017 Jackson .................. A61N 5/10
(Continued)

FOREIGN PATENT DOCUMENTS

WO    WO 2008/003526 A2    1/2008
WO    WO 2008/003527 A1    1/2008
WO    WO 2010/101489 A1    9/2010

*Primary Examiner* — David A Vanore
(74) *Attorney, Agent, or Firm* — Finnegan, Henderson, Farabow, Garrett & Dunner LLP

(57) ABSTRACT

The present disclosure relates to a particle therapy system for irradiating a target with a scanning beam technique. In one implementation, the system includes an irradiation planning device with a planning algorithm configured to associate a particle beam energy E(i) to each spot of the irradiation plan and organize the spots in a sequence of spots according to energy. The system may further include a control system configured for controlling in parallel, from spot to spot, a variation of an output energy of a beam generator, a variation of a magnetic field of one or more electromagnets of a beam transport system and a variation of a magnetic field of the scanning magnet.

16 Claims, 10 Drawing Sheets

(51) Int. Cl.
*H05H 13/02* (2006.01)
*H05H 13/04* (2006.01)

(52) U.S. Cl.
CPC ....... *H05H 13/04* (2013.01); *H05H 2007/048* (2013.01); *H05H 2245/122* (2013.01)

(56) References Cited

U.S. PATENT DOCUMENTS

| | | | | |
|---|---|---|---|---|
| 9,776,017 | B2* | 10/2017 | Flynn | A61N 5/1043 |
| 2010/0320403 | A1* | 12/2010 | Amaldi | A61N 5/10 |
| | | | | 250/492.3 |
| 2014/0087953 | A1* | 3/2014 | Bromberg | H05H 7/00 |
| | | | | 505/200 |
| 2016/0199667 | A1* | 7/2016 | Flynn | A61N 5/1043 |
| | | | | 600/1 |

* cited by examiner

Fig. 4 (Invention)

PARTICLE THERAPY SYSTEM AND METHOD WITH PARALLEL CONTROL OF ENERGY VARIATION AND BEAM POSITION VARIATION

This application claims the benefit of priority of European Patent Application No. 15199614.1, filed Dec. 11, 2015, the subject matter of which is incorporated herein by reference in its entirety.

FIELD OF THE INVENTION

The invention is related to the field of particle therapy systems for irradiating a target with a scanning technique. Such a particle therapy system comprises a particle beam generator for generating a particle beam, a beam transport system for transporting the particle beam from the particle beam generator to a treatment location and a scanning device located downstream of the beam transport system. The scanning device comprises one or more scanning magnets configured for varying the position of the particle beam over the target. The beam generator is operable to vary an output energy of the particle beam. In one example, the beam generator comprises a fixed-energy cyclotron or a fixed-energy synchrocyclotron accelerator combined with an energy degrader configured to vary the fixed energy of the beam of the cyclotron or synchrocyclotron. In another example, the beam generator comprises a synchrotron accelerator operable to vary the acceleration energy.

Typically, for proton particles, the output energy of the particle beam generator for use in particle therapy can vary between 70 MeV and 250 MeV. Other examples of particles used for particle therapy are carbon ions or other light ions.

A particle therapy system also comprises an irradiation planning device that is configured for generating an irradiation plan or treatment plan. Typically, an irradiation planning device is a computer based device using algorithms or calculation engines and patient computed tomography (CT) data sets to define the treatment plan. The plan defines parameters for the therapy system so as to deliver the planned particle dose at the planned location in the target. The particle therapy system generally comprises a control system configured for receiving the irradiation plan from the planning device and configured for controlling the irradiation of the target according to the irradiation plan.

The invention also relates to a method to irradiate a target or a phantom.

BACKGROUND OF THE INVENTION

When applying a scanning technique, a particle beam is magnetically scanned over a target. By varying the energy of the particle beam, different depths in the target volume can be reached. In this way, particle radiation dose can be delivered to the entire 3D target volume.

In current practice, irradiation planning devices for scanning techniques divide the delivery of the beam to a target in mono-energetic sections or layers.

The irradiation planning device defines the number of layers to be irradiated and for each layer a corresponding beam energy is defined. For each layer, the planning device typically defines a number of spots wherein each spot is defined by a dose $D(i)$ and a beam position defined by coordinates $X(i)$, $Y(i)$. The coordinates correspond to the coordinates of the beam position in a plane perpendicular to the un-scanned beam.

In FIG. 3, a diagram is shown indicating the steps performed by well known irradiation planning devices and beam delivery systems. For such known systems, in step A, a number of spots are planned and the spots are grouped in a number of layers wherein each layer comprises spots of equal energy. In step B the plan is transmitted to the control system of the beam delivery system. Further, when performing an irradiation in step C, the output energy of the particle beam generator and the electromagnets of the beam transport system are set according to the energy of a first layer. Then step D is performed after step C is completed. In step D, the scanning magnets are set to position the beam to a first planned position $X(1)$, $Y(1)$ corresponding to the first spot of the first layer. Then in a step E, performed after completion of step D, the beam is turned on to deliver the planned dose to the first spot of the first layer. Thereafter, as an iterative process, step D and step E are repeated until all spots of the first layer have been irradiated. Finally, one restarts with step C going to the next layer and one iterates until all layers have been irradiated. In other words, in this scenario, the control of the variation of the output energy of the beam generator and control of the variation of the magnetic field of the scanning magnets is performed in series.

With the currently known systems, typically, the beam delivery system will follow a spot order that corresponds to for example a raster scan, wherein the beam is scanned for example from left to right and up and down. So with the well known devices, it is a scanning pattern that will define the order of the spots to be irradiated. There is also no specific order of the layers defined or imposed, the beam delivery system can execute the irradiation of the layers in any order.

This change of energy in-between layers takes some precious time during which no irradiation can be performed. The reason this energy change takes considerable time is related to a number of causes such as the inertia of mechanical devices that have to be moved as a function of energy (for example an energy degrader), the power supplies for the electromagnets of the beam transport system have limits in terms of how fast the currents can be changed, the magnetic field in the beam transport system is influenced by eddy currents impacting the time to settle the required magnetic field in the beam line, when superconducting electromagnets are used currents can only be changed slowly to avoid quenching. Furthermore, the reduction of time required to change energy is expensive due to the fact that devices with significant inertia (both mechanical devices and currents in electromagnets) need to be adapted.

SUMMARY OF THE INVENTION

It is an object of the present invention to reduce the total irradiation time of a particle therapy scanning system at reasonable cost.

This objective is accomplished by the device and method according to the invention as defined by the independent claims. The dependent claims relate to preferred embodiments.

According to a first aspect of the invention, a particle therapy system for irradiating a target with a scanning beam technique is provided.

Such a system comprises an irradiation planning device configured for generating an irradiation plan for irradiating the target with the scanning technique. The plan comprises a number of spots wherein each spot has an associated beam position and wherein each spot has an associated dose $D(i)$ or a parameter related to a dose.

The system further comprises a particle beam generator for generating a particle beam and operable to vary an output energy, a beam transport system, comprising one or more electromagnets, for transporting the particle beam from the particle beam generator to a treatment location, a scanning device comprising one or more scanning magnets configured for varying the position of the particle beam over the target, a control system configured for receiving the irradiation plan from the planning device and configured for delivering and controlling the irradiation of the target according to the irradiation plan.

The particle therapy system according to the invention is characterised in that the irradiation planning device or the control system comprises a planning algorithm configured to associate a particle beam energy E(i) to each spot of the irradiation plan and to organize the spots in one or more sequences of spots according to the associated particle beam energy. Further, the control system is configured for irradiating the target following the order of the spots in the one or more sequences of spots and the control system comprises process control means configured for controlling in parallel
   a) a variation of an output energy of the particle beam generator, wherein the variation of the output energy corresponds to a variation of the spot energy between two consecutive spots from E(i) to E(j),
   b) a variation of a magnetic field of the one or more electromagnets of the beam transport system, wherein the variation of the magnetic field corresponds to the variation of the beam spot energy between two consecutive spots from E(i) to E(j),
   c) a variation of a magnetic field of the one or more scanning magnets of the scanning device, wherein the variation of the magnetic field corresponds to the variation of the beam spot energy between two consecutive spots from E(i) to E(j) and/or to a variation of the beam position between said two consecutive spots.

Indeed, by associating an energy to each spot, organizing the spots in a sequence according to energy and controlling in parallel output energy variations and associated magnetic field variations, the total time need to perform the irradiation of all spots can be reduced. By associating an energy to each spot, instead of associating an energy to a group or layer of spots, the overall energy variation from the minimum beam energy to the maximum beam energy needed to perform the irradiation, can be spread out over more spots and hence large time-consuming energy variations between groups or layers of spots can be avoided.

Preferably, the planning algorithm is configured to organize the spots in each sequence of the one or more sequences of spots, such that the particle beam energy E(i) associated to each spot is an increasing or decreasing monotonic function. The additional advantage of such order of the spots in the sequence is that Eddy currents in the electromagnets can be strongly reduced.

More preferably, the planning algorithm is configured to associate the particle beam energy E(i) to the spots such that the variation of the particle beam energy between two consecutive spots of said one or more sequences of spots remains below a given maximum value. In this way one can avoid that energy changes between two beam positions are too large.

In preferred embodiments, the particle therapy system according to the invention has a beam transport system that comprises a gantry device and wherein the one or more electromagnets are installed in the gantry device.

Typically, when using a gantry device, multiple electromagnets are used and the magnetic field of these magnets needs to be adjusted for each output energy variation. With the solution of the invention, using parallel control as defined above, the overall time needed to perform these variations is reduced.

According to a second aspect of the invention, a method is provided for irradiating a target or a phantom with a particle beam scanning technique, the method comprising steps of
   preparing an irradiation plan comprising steps of
      a) defining a number of spots wherein each spot has an associated beam position,
      b) associating to each spot a dose D(i) or a parameter related to a dose,
      c) associating a particle beam energy E(i) to each spot,
      d) organizing the spots in one or more sequences of spots according to the beam energy associated to each spot,
   providing a particle beam generator configured for generating a particle beam and operable to vary an output energy,
   providing a beam transport system for transporting the particle beam from the particle beam generator to a treatment location, said beam transport system comprising one or more electromagnets,
   providing a scanning device comprising one or more scanning magnets configured for varying the position of the particle beam over the target,
   irradiating the target following the order of the spots in the sequence of the one or more sequences of spots and using a control system configured for controlling in parallel
      a) a variation of an output energy of the particle beam generator, wherein the variation of the output energy corresponds to a variation of the spot energy between two consecutive spots from E(i) to E(j),
      b) a variation of a magnetic field of said one or more electromagnets of the beam transport system, wherein the variation of the magnetic field corresponds to the variation of the beam spot energy between two consecutive spots from E(i) to E(j),
      c) a variation of a magnetic field of the one or more scanning magnets of the scanning device, wherein the variation of the magnetic field corresponds to the variation of the beam spot energy between two consecutive spots from E(i) to E(j) and/or to a variation of the particle beam position between the two consecutive spots.

With this method, by preparing the irradiation plan as a sequence of spots organized according to energy and using a control system with parallel controls, the overall irradiation time is reduced.

Preferably, according to the method of invention, the irradiation plan is prepared such that for each sequence of the one or more sequences of spots, the spot energy E(i) is an increasing or decreasing monotonic function.

SHORT DESCRIPTION OF THE DRAWINGS

These and further aspects of the invention will be explained in greater detail by way of example and with reference to the accompanying drawings wherein.

Figure 5:
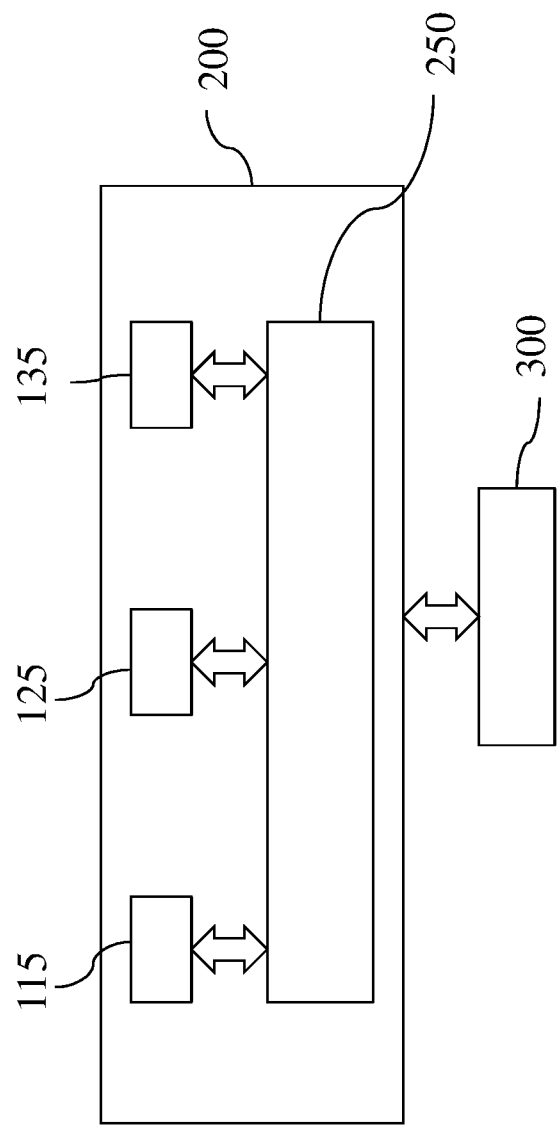
Figure 6:
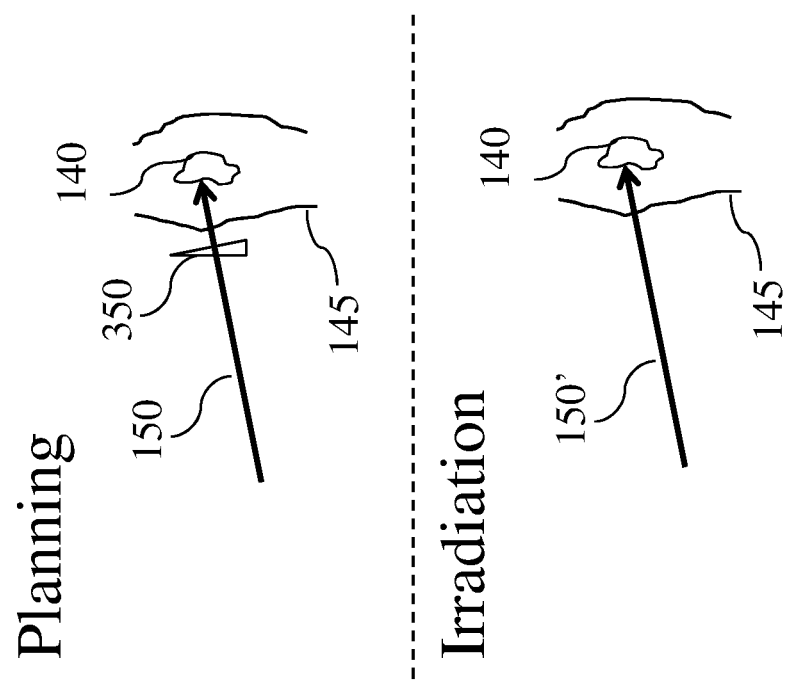
Figure 7:
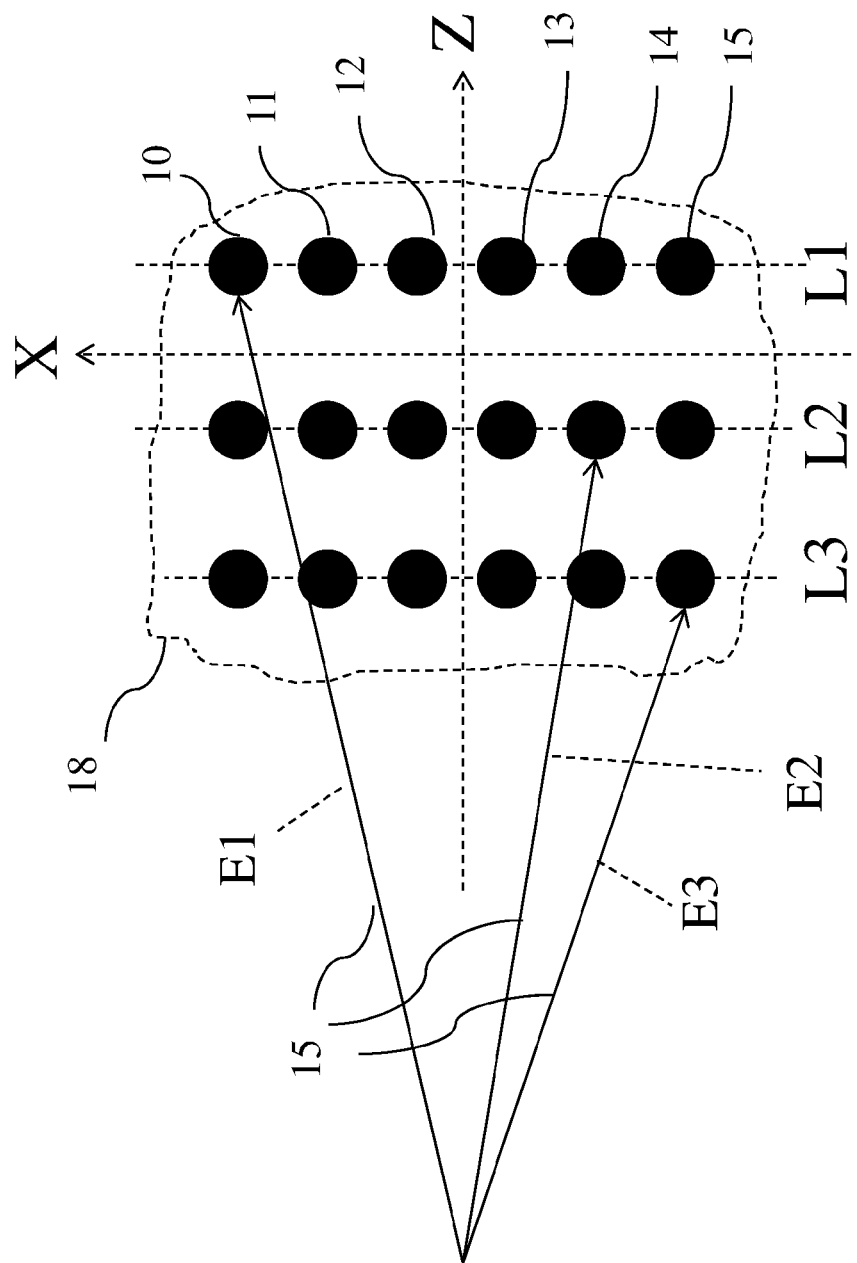
Figure 8:
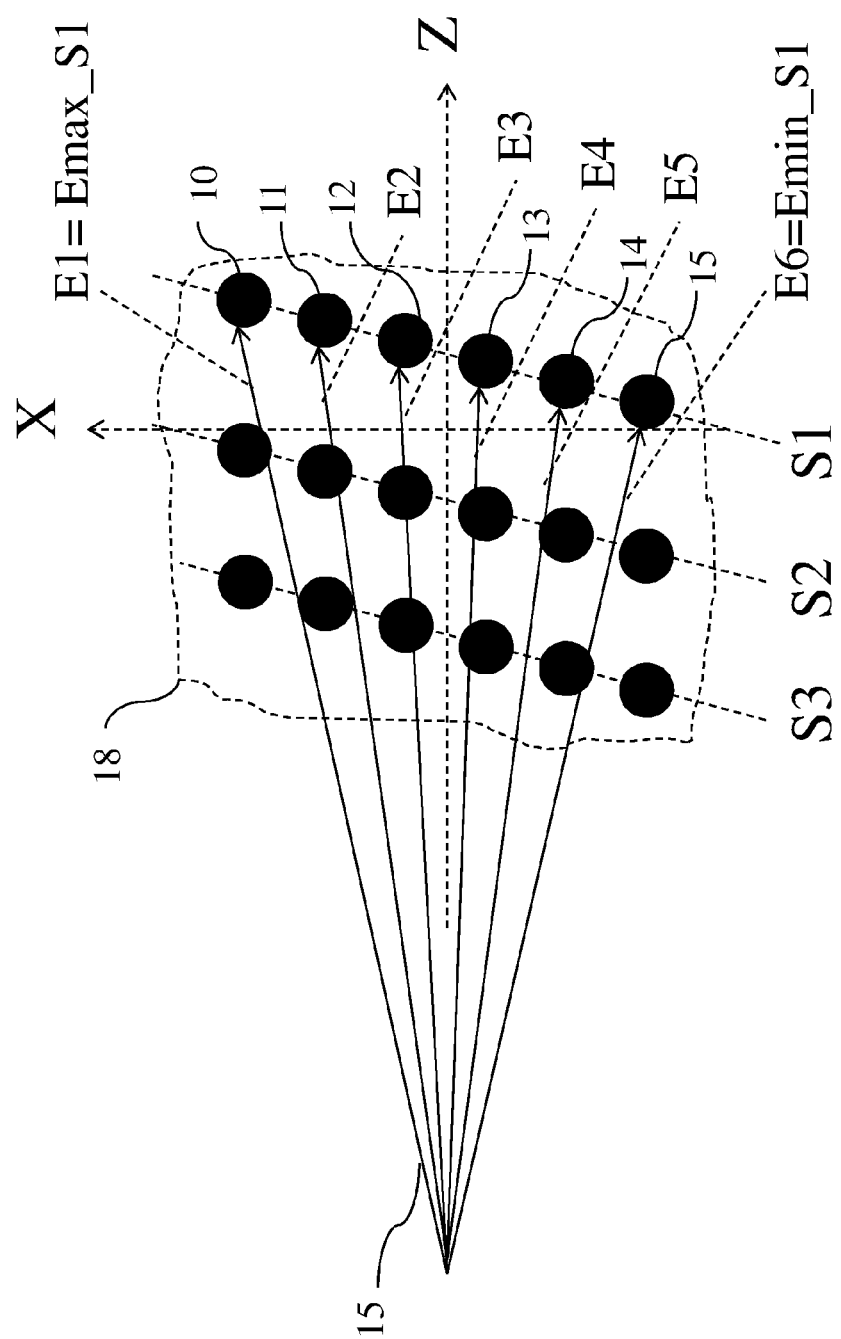
Figure 9:
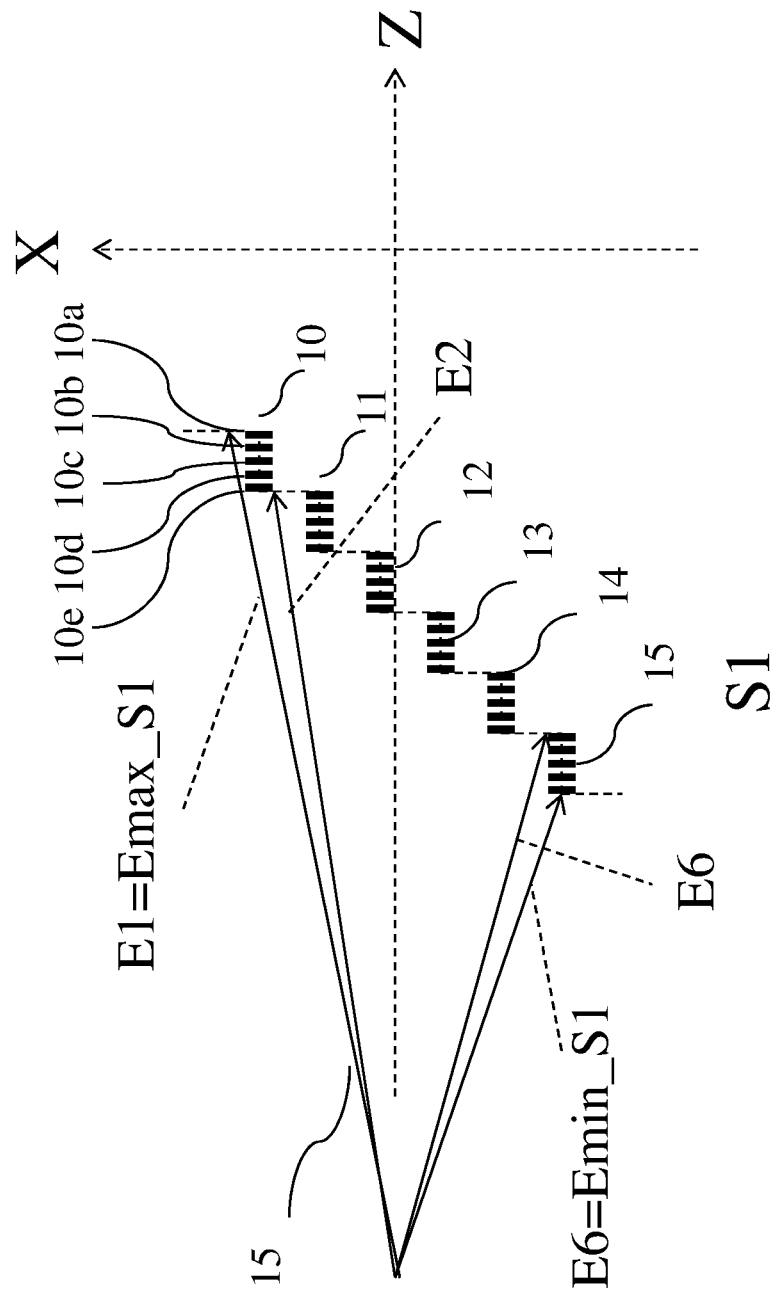
Figure 10:
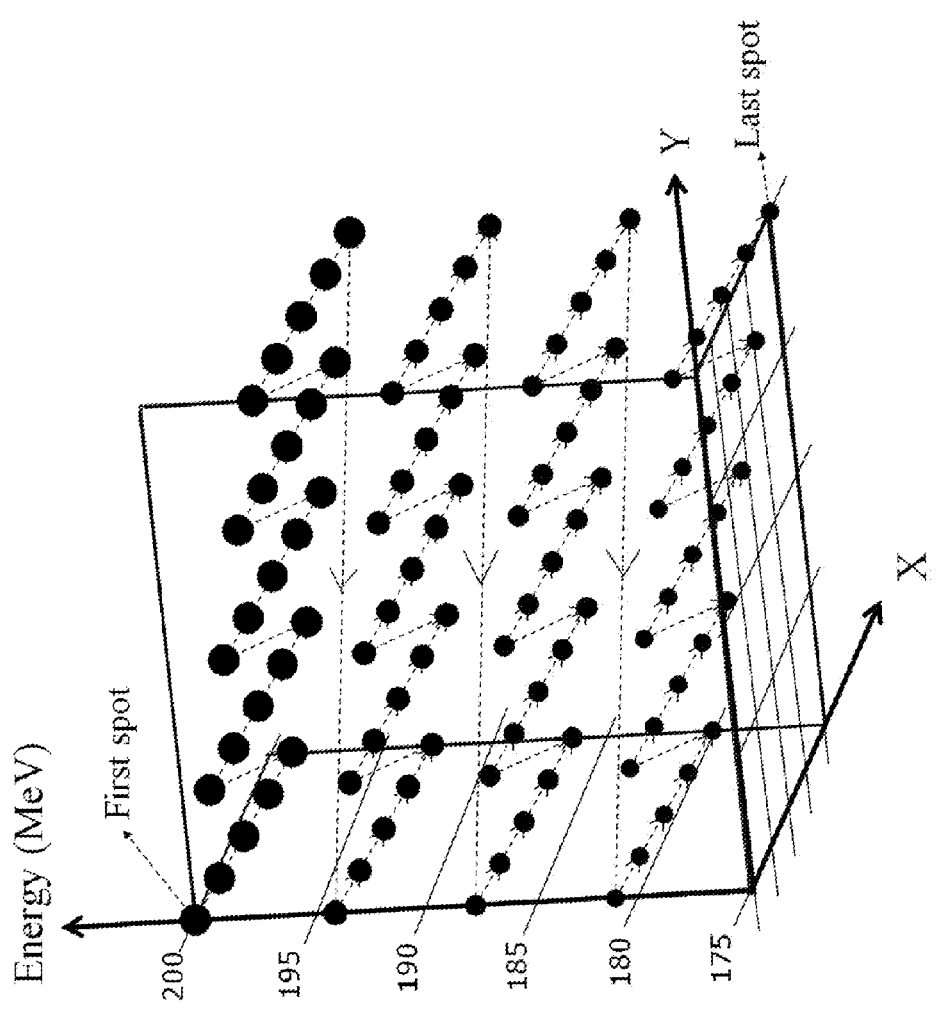

FIG. 5 schematically illustrates a control system according to the invention;

FIG. 6 shows a schematic presentation of the use of a virtual wedge;

FIG. 7 illustrates an intermediate sequence of spots grouped in layers comprising spots of the same energy;

FIG. 8 shows sequences of spots according to the invention;

FIG. 9 shows a another example of a sequence of spots according to the invention;

FIG. 10 shows a schematic representation of a sequence of spots according to the invention.

The figures are not drawn to scale. Generally, identical components are denoted by the same reference numerals in the figures.

DETAILED DESCRIPTION OF PREFERRED EMBODIMENTS

According to a first aspect of the invention, a particle therapy system is provided for irradiating a target with a scanning technique. The particle therapy system comprises a planning device for defining an irradiation plan and a beam delivery system for executing the irradiation plan.

Figure 1:
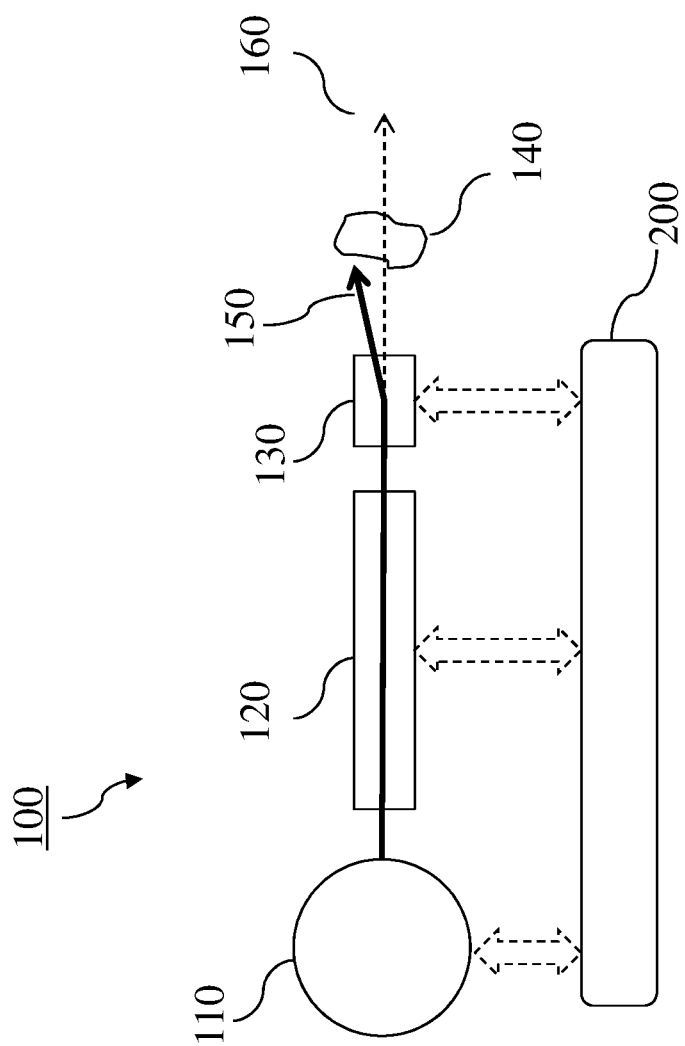
FIG. 1 shows a beam delivery device according to the invention.

An example of a beam delivery system 100 according to the invention is shown in FIG. 1. The beam delivery system comprises a beam generator 110 for outputting a particle beam and operable to vary an output energy, a beam transport system 120 for transporting the particle beam from the beam generator to a treatment location, a scanning device 130 for scanning the particle beam over the target 140 and a control system 200 configured for receiving the irradiation plan from the planning device and configured for delivering and controlling the irradiation of the target according to the spots of the irradiation plan.

Typically, the control system comprises sub-controllers configured for controlling the particle beam generator, controlling the beam transport system and controlling the scanning device.

The beam generator 110 can either be a synchrotron that is operable to vary the energy of the beam extracted out of the synchrotron or the beam generator can be a fixed-energy accelerator, such as a cyclotron or a synchrocyclotron, combined with an energy degrader. Such an energy degrader is configured to degrade the energy of the beam extracted out of the fixed-energy accelerator. A beam generator that comprises a cyclotron and a mechanically rotating energy degrader is for example disclosed in EP1145605. To vary an output energy of the particle beam generator having an energy degrader, the degrader needs to be moved mechanically to a different energy position.

The beam transport system comprises one or more electromagnets. Typically, the beam transport system comprises one or more dipole and quadrupole electromagnets. The beam transport system is configured to transport the beam from the beam generator to the target to be irradiated.

In an exemplary embodiment, the beam transport system comprises a gantry device which allows to irradiate a target from different directions.

In another exemplary embodiment, the particle therapy system comprises a patient positioning device and the process control means are configured to control in parallel a variation of the output energy of the particle beam generator and a variation of a position of the patient positioning device.

The scanning device is located downstream of the beam transport system. A scanning device according to the invention comprises one or more scanning magnets configured for scanning the particle beam 150 over the target 140 or, in other words, by varying the magnetic field of the one or more scanning magnets, the beam position of the particle beam on the target is varied. The position of the beam on the target is generally defined by coordinates X(i),Y(i) corresponding to coordinates of a position of the beam in a plane perpendicular to an un-scanned beam direction 160. This plane being defined by two axes X and Y. The un-scanned beam direction 160, shown on FIG. 1, is typically the direction of the beam when the scanning magnets of the scanning device are off. By defining a sequence of spots with spot positions (X(i), Y(i)) a scanning trajectory is defined for scanning the beam over the target by having the beam moved from one spot to the next spot in the sequence. Many types of scanning techniques exist. There is the so-called spot scanning technique where the scanning magnets are set for directing the beam to a given spot position. Then a prescribed dose to the spot is delivered and when the spot dose is delivered the beam is shut off and the scanning magnets are then set for moving the beam to the next spot.

Another type of scanning technique is the so-called raster scanning technique where the beam is not shut off after a spot irradiation. With this technique, the beam is delivered to a spot and when the dose is reached the beam is quickly moved to the next spot without shutting off the beam. In a third example of a scanning technique which is the continuous scanning technique, the intensity of the beam is continuously varied while scanning the beam over the target following the pre-defined trajectory.

The particle therapy system according to the invention may apply a spot scanning technique, a raster scanning technique, a continuous scanning technique or any other type of scanning technique.

The particle therapy system according to the invention comprises an irradiation planning device 300 that is configured for generating an irradiation plan for irradiating the target with a scanning technique.

For a particle therapy system using a scanning technique, such an irradiation planning device is defining a plan comprising a number of spots and wherein each spot has a number of parameters associated such as the particle beam energy E(i) and an associated beam position. In general, such a beam position is defined by two parameters X(i) and Y(i) that correspond to coordinates of a position of the beam in a plane perpendicular to an un-scanned beam direction 160. In addition, each spot has an associated dose D(i) or a parameter related to a dose. Such a parameter can for example be a parameter proportional to the dose such as so-called monitor units to be delivered or the parameter can be expressed as a number of particles to be delivered or a number of charge to be delivered.

When, according to the irradiation plan, the particle beam energy associated to a spot is planned to change from one spot to another, a number of parameters of the particle beam delivery system need to be varied in order to support this change of beam energy. The major parameter settings that need to be varied when varying the particle beam energy are the output energy of the particle beam generator, the magnetic field of one or more electromagnets in the beam transport system and the magnetic field of the scanning magnets of the scanning system. The relation between particle beam energy, generally expressed in MeV (mega electron volts) and the corresponding parameter settings are well known and are straightforward to calculate or to define.

Typically, the irradiation planning device comprises a computer or workstation. As shown on FIG. 2, the irradiation planning device 300 interfaces with the control system 200 of the beam delivery system. The control system 200 is configured to receive the irradiation plan from the irradiation planning device.

The control system 200 is further configured for controlling the irradiation of the target according to the irradiation plan. This means that the control system assures that the parameters defined in the plan are correctly applied so as to deliver the right dose to the right location in the target.

The irradiation planning device 300 according to the invention comprises a planning algorithm configured to associate a particle beam energy E(i) to each spot of the irradiation plan and organize the spots in one or more sequences of spots according to the associated particle beam energy.

In other words, the order of the spots in a sequence is determined based on the energy associated to the spot. For example, the spots can be ordered in a sequence such that the particle beam energy E(i) for consecutive spots is an increasing or decreasing monotonic function.

In FIG. 10, a schematic representation is shown of an exemplary spot sequence provided by a planning device according to the invention. The dots on the figure represent spots and the diameter of the dots is proportional with the dose D(i) associated to each spot. On the figure the first point and the last point of a sequence of spots are indicated. The spots are connected by dotted lines to illustrate the order of the spots in the sequence. The beam position associated to each spot is defined by the coordinates X,Y and each spot has an associated particle beam energy E(i). In this example, the associated particle beam energy of the spots is expressed in MeV (mega electron volts) and the beam energy associated to each spot in the sequence varies from 200 MeV for the first spot to 175 MeV for the last spot.

In the example of the spot sequence shown in FIG. 10, the spot energy E(i) is a strict decreasing monotonic function from 200 MeV down to 175 MeV. However, the invention is not limited to a strict monotonic decreasing energy function (or a strict monotonic increasing energy function), the sequence can for example comprise subsequent spots having the same associated energy.

As mentioned above, the control system 200 is configured for executing the irradiation plan, i.e. the control system is configured for irradiating the target following the order of the spots in the one or more sequences of spots.

Figure 2:
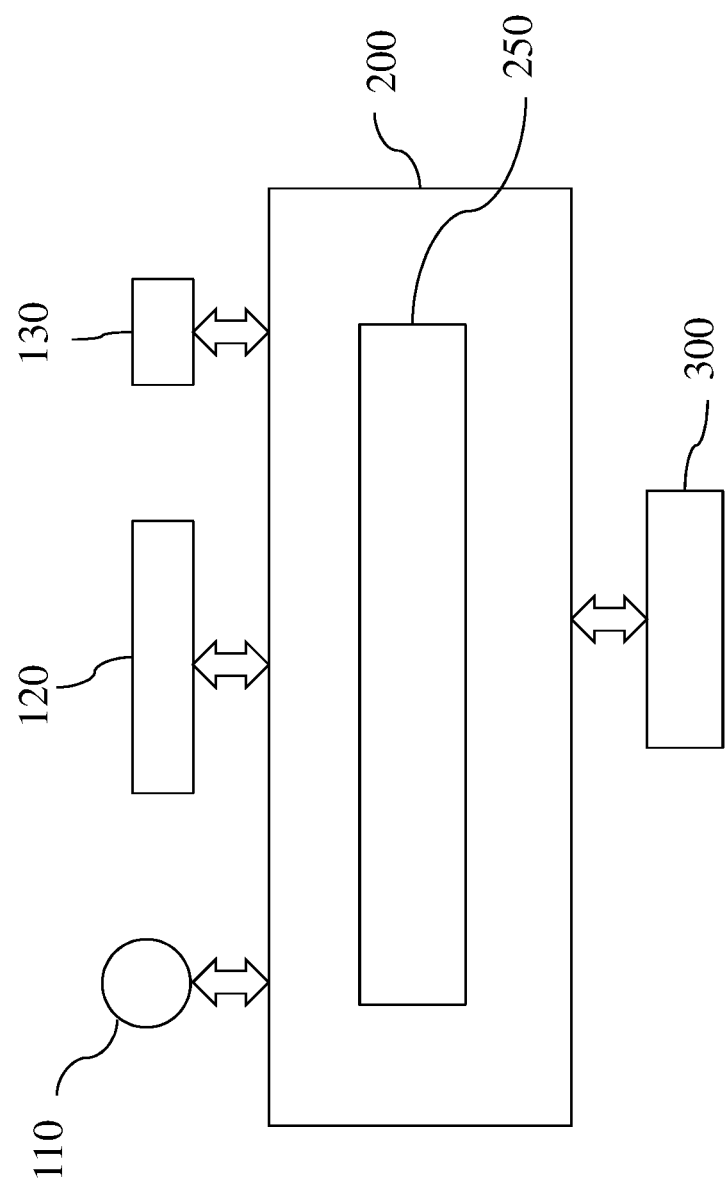
FIG. 2 shows a schematic representation of a particle therapy system according to the invention.
Figure 3:
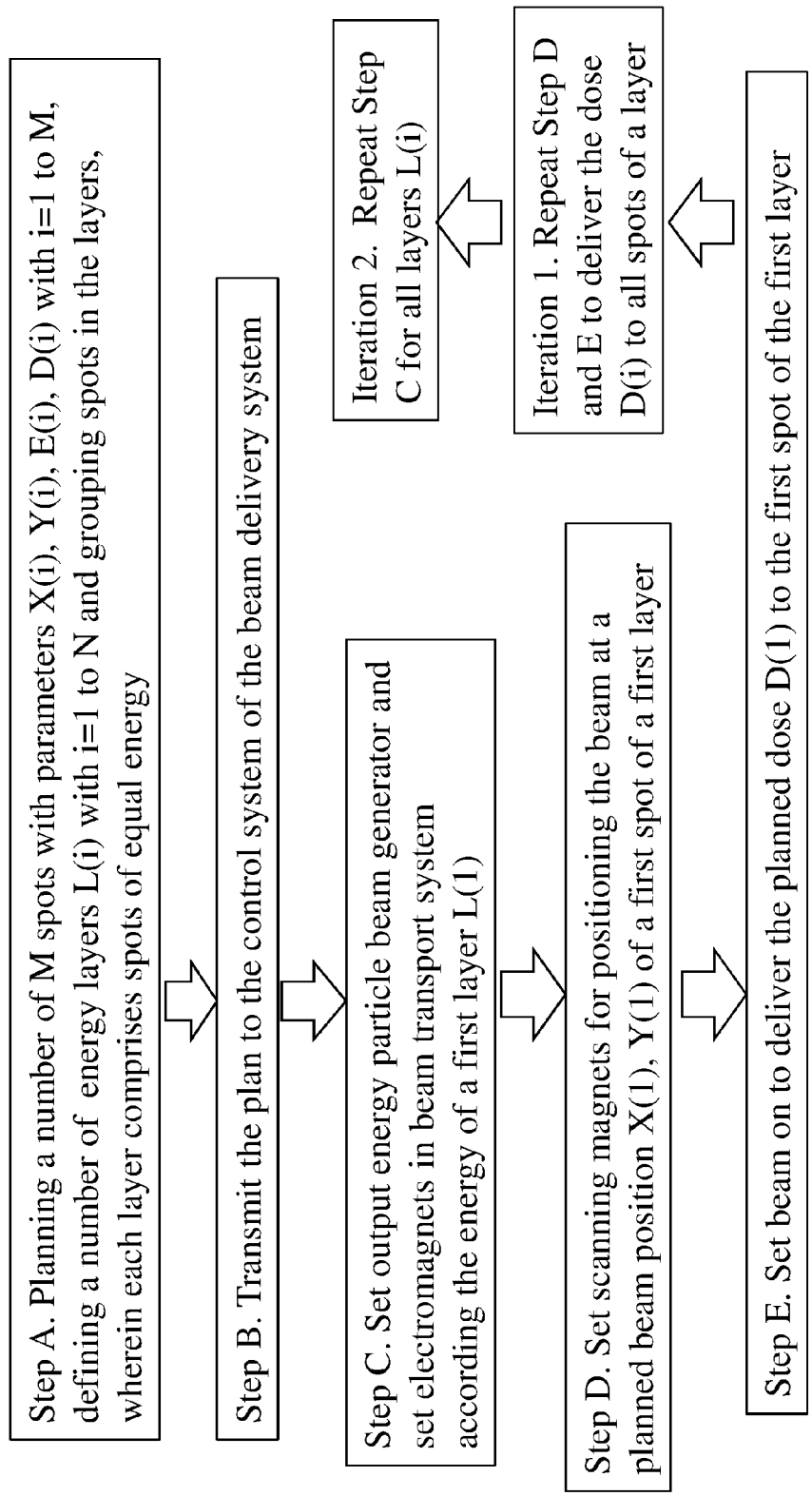
FIG. 3 shows a schematic presentation of steps followed by a control system according to the known background art.

As shown in FIG. 2, the control system 200 comprises process control means 250. The process control means 250 are configured for controlling in parallel a) a variation of an output energy of the particle beam generator, wherein the variation of the output energy corresponds to a variation of the spot energy between two consecutive spots from E(i) to E(j), b) a variation of a magnetic field of said one or more electromagnets of the beam transport system, wherein the variation of the magnetic field corresponds to the variation of the beam spot energy between two consecutive spots from E(i) to E(j), c) a variation of a magnetic field of the one or more scanning magnets of the scanning device, wherein the variation of the magnetic field corresponds to the variation of the beam spot energy between two consecutive spots from E(i) to E(j) and/or to a variation of the beam position between the two consecutive spots.

This parallel control of a variation of the output energy, a variation of one or more electromagnets and the variation of one or more scanning magnets is not existing in the particle therapy systems developed so far, where, as discussed above, those steps are performed in sequence.

Figure 4:
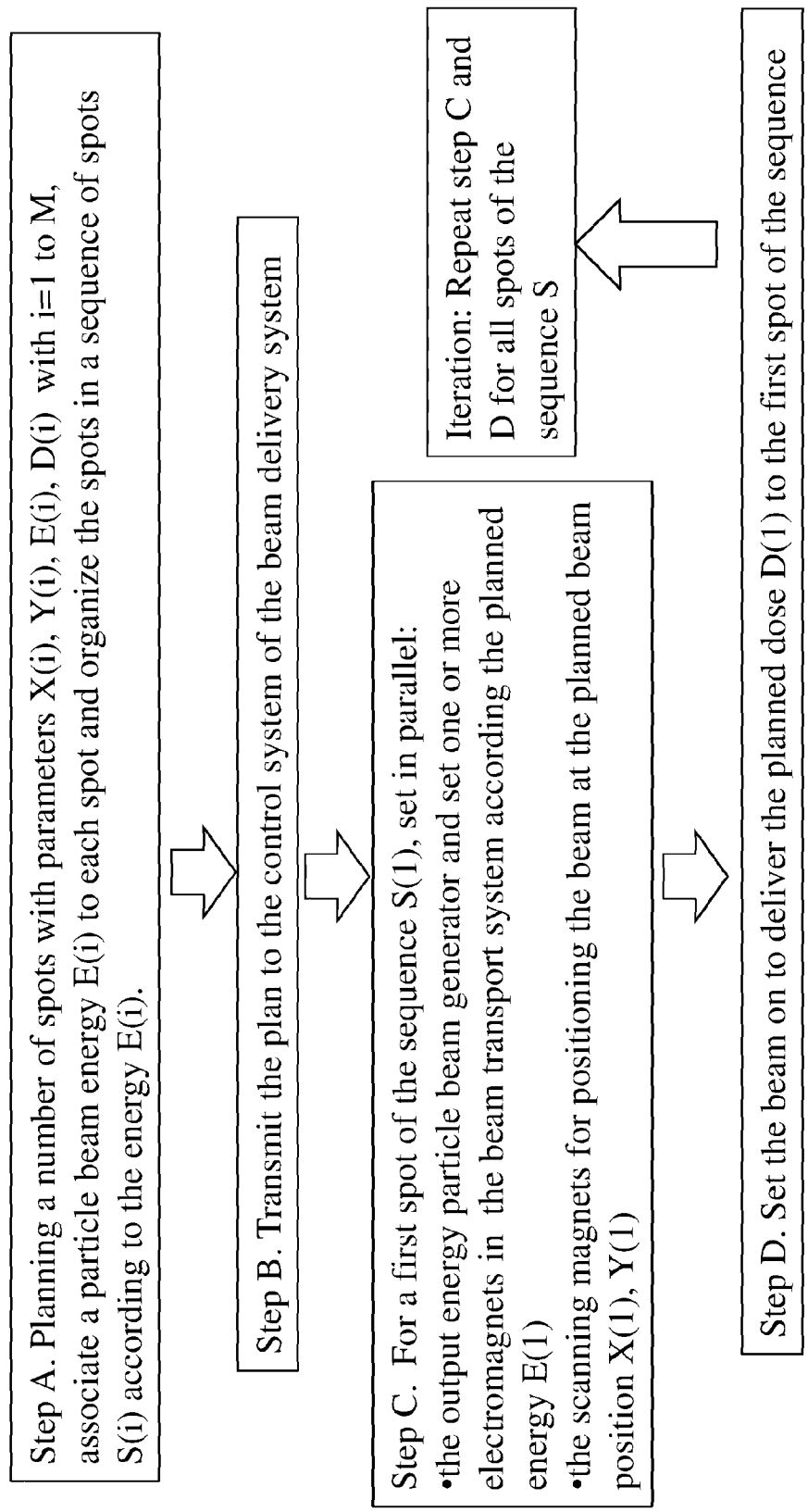
FIG. 4 shows a schematic presentation of steps followed by a control system according to the invention.

In FIG. 4, the typical steps performed by the planning device and the beam delivery system according to the invention are illustrated. In a first step A, a number of spots are planned and a particle beam energy E(i) is associated to each spot and the spots are organized in a sequence according to the energy associated to each spot. For example, the spots are ordered in the sequence such that the energy of the spots in the sequence is an increasing or decreasing monotonic function. In step B, the plan is transmitted to the control system of the beam delivery system. Further, in step C, when ready for performing the irradiation for a first spot of the sequence, the output energy of the beam generator, the magnetic field of the electromagnets of the beam transport system and the magnetic field of the scanning magnets are set in parallel for the first spot. Thereafter, in step D, the beam is turned on to deliver the planned dose to the first spot of the sequence. As an iterative process, steps C and D are repeated for all spots of the sequence. For the embodiment where more than one sequence is defined on the planning level, there is an additional step, not shown on FIG. 4, to iterate and restart at step C to perform the irradiation of the other sequences.

In other words, according to the invention all parameters related to a spot, including the spot energy, are controlled from spot to spot. In contrast to the prior art control systems where there is a control on a layer per layer basis. The advantage of this method according to the invention, as outlined in FIG. 4, is that the total irradiation time can be reduced. Indeed, as in step C, the parameter settings of beam generator, electromagnets and scanning magnets are set in parallel, the overall time to set the parameter is reduced. Also, as on the planning level, an energy is associated to each spot and the spots are ordered logically according to an increasing or decreasing monotonic function, the overall energy variation of the particle beam is spread over more spots, hence reducing the presence of large energy variations from spot to spot. Effects such as eddy currents in the electromagnets are hereby avoided or strongly reduced.

According to a preferred embodiment of the invention, the planning algorithm is configured such that for each sequence of the one or more sequences of spots, the variation of particle beam energy between two consecutive spots remains below a given maximum value.

This given maximum value is related to parameter constraints of the beam delivery system 100. More precisely, the given value is related to a maximum speed to vary the output energy of the particle beam generator and/or a maximum speed to vary a magnetic field of said one or more electromagnets in the beam transport system.

Preferably, the given value is a value equal or lower than 5%. More preferably, the pre-defined value is a value equal or lower than 2%.

In other words, according to this preferred embodiment, the algorithm of the planning device is developed to take into account specific parameter constraints from the beam delivery system. The constraints are related to the time it requires to change the parameter settings of the beam delivery system when the energy of the beam needs to be varied.

By limiting the variation of energy from spot to spot, i.e. by allowing only small energy variations, it will take less time to set the corresponding parameter settings for a small energy variation than for a large one and effects of hysteresis of the electromagnets are further reduced.

There are a number of different types of process control means that can be used to perform the functions according to the invention.

In a first example, the process control means correspond to a control processor that is configured to perform a closed loop control. This control processor 250 receives feedback information from the particle beam generator, the beam transport system and from the scanning device. More particular, the control processor receives status information related to the output energy of the generator, status information related to the magnetic field of one or more electromagnets of the beam transport system and status information related to the magnetic field of one or more scanning magnets.

An example of control system 200 is schematically shown in FIG. 5. In this example, the control processor 250 interfaces with the beam generator controller 115, the beam transport controller 125 and the beam scanning controller 135. The interfaces can be performed through a fast communication channel (e.g. Ethernet) or field bus (e.g. Profibus). The control system 200 receives a plan from the planning device 300 which comprises as discussed above a sequence of spots. When a spot energy changes from one spot to the other, the control processor will control the simultaneous variation of the energy of the generator, the variation of the magnetic field of one or more electromagnets of the beam transport system and the variation of the magnetic field one or more scanning magnets of the scanning device.

In another example, the process control means 250, correspond to a control processor that is configured to perform an open loop control. For example, the control processor comprises a clock signal generator that is configured to generate and share a clock signal between the various sub-control units of the control system. Sub-control units can for example be the beam generator controller 115, the beam transport controller 125 and the beam scanning controller 135. In this way, these various sub-units are synchronized through a common clock signal.

In a further example, the process control means comprises a speed controller configured to adapt the speed for varying the energy of the generator, or adapt the speed for varying the magnetic field in the electromagnets of the beam transport system or adapt the speed for varying the magnetic field of the scanning magnets. In this example, the speed controller is configured to adapt the speed to vary certain parameters according to the slowest device. For example, suppose that the variation of the magnetic field in one or more electromagnets of the beam transport system is the slowest process, then the speed controller can adjust the speed to vary the output energy of the beam generator and adjust the speed to vary the magnetic field of the one or more scanning magnets according the slow variation of the magnetic field of the beam transport electromagnets.

In another example, the process control means is a process controller that sends simultaneously command controls to the various sub-control units such as for example the beam generator controller 115, the beam transport controller 125 and the beam scanning controller 135. The process controller then monitors the feedback status of the various sub-control units and when status information is received indicating that the particle generator, the beam transport system and the scanning device are correctly set and ready for the irradiation of a next spot, a signal is outputted to an irradiation controller to start the irradiation of the next spot.

To illustrate the advantage with respect to the overall irradiation time when using this control system according to the invention, an example is provided.

Consider first a classical irradiation plan, known in the art, where a target is divided into 15 iso-energetic layers and wherein each layer comprises 100 spots. So in total there are 15×100=1500 spots to be irradiated. To each spot is also associated a beam position (sometimes also named the spot position) and a dose. The time needed to change the energy from one layer to the other takes 1 second (this is for a typical change of energy corresponding to a 10 mm change of range in a water target). In this example, 14 energy changes need to be performed. The typical spot irradiation time to deliver the dose is 3 ms (millisecond) and the average change of beam position from spot to spot takes 3 ms. So using this classical irradiation plan with a classical control system, the total irradiation time to irradiate each spot of all 15 layers will be the sum of the time needed to change layer energies, the time to deliver the dose for each spot and the time to change the beam position from spot to spot: 14×1 s+15×100×0.003 s+15×99×0.003 s=23 s.

As a comparison, the irradiation of the same exemplary target is considered with a particle therapy system according to the invention. This system has an irradiation planning device with a planning algorithm configured to associate a particle beam energy E(i) to each spot and to organize the spots in a sequences of spots and the system further comprises a control system with parallel control according to the invention. In this example, we again consider 15×100=1500 spots and each spot has the same beam position and dose associated as in the above example using a classical plan. The difference here compared to the classical example discussed above, is that there is an energy associated to each spot such that the energy is changing in small steps from spot to spot. The spots are grouped in one sequence instead of grouped in energy layers. Assume that the small energy change from spot to spot correspond to a 0.1 mm (millimeter) of change of range in a water target. With the parallel control system according to the invention, the energy changes are performed in parallel with the change of beam position. In this example, it is assumed that this combined energy change and position change takes 5 ms, to compared with the 3 ms when only a position change is made without an energy change. With this example, as there is an energy change from spot to spot, there are in total 1499 energy changes to be performed. Hence, with the system according to the invention, the total irradiation time to irradiate the 1500 spots will be the sum of the time to deliver the dose for each spot and the time to vary in parallel the energy and the beam position from spot to spot: 1500×0.003 s+(1500−1)× 0.005 ms=12 s. This illustrates that for irradiating a same target volume with the same number of spots, with the particle therapy system according to the invention, the total irradiation time is reduced by almost a factor of two when compared to a classical approach.

As discussed above, the planning device according to the invention comprises an algorithm configured to associate a particle beam energy E(i) to each spot and to organize the spots in one or more sequences of spots and wherein for each sequence of spots of the one or more sequences of spots, the spot energy E(i) is an increasing or decreasing monotonic function.

In contrast, the prior art planning algorithms defines energy layers and by definition the spots in a layer adopt the energy of the layer. There is no association of a particle beam energy from spot to spot as part of an overall planning optimization that can support the reduction of the irradiation time.

There are a number of different ways to implement the planning algorithm according to the invention. Four examples will be discussed.

First Example Algorithm of Planning Device:

A first example of an algorithm of the irradiation planning device according to the invention will now be further described. In a first step an intermediate plan taking into account the presence of a wedge shaped element located upstream of the target is made. In a second step a final plan to irradiate the target without the wedge by adjusting the particle beam energy E(i) of the spots of the intermediate plan. To make this adjustment of the energies of the spots geometrical characteristics of the wedge shaped element are taken into account.

This wedge shaped element 350 taking into account by the planning device is virtual in the sense that it is only used during the planning phase by the irradiation planning device and it is not used during the irradiation phase by the beam delivery system. The energy of the beam is changed depending of the position where the particle beam 150 enters the wedge-shaped element.

In the planning phase, in the first step a virtual wedge 350 is put in front of the target 140 to be irradiated as shown in the top part of FIG. 6. As shown on FIG. 6, the virtual wedge is located upstream of the target. Upstream has to be construed as upstream with respect to the direction of the beam 150 direction. The target 140 is for example a tumor volume to be irradiated located in a patient. On FIG. 6, the surface 145 of the patient's body is indicated. Either a CT scan can be taken of the target together with a real physical wedge or a virtual wedge can be added by software on the planning image.

The geometrical characteristics of the wedge shaped element, such as dimension and variation of the thickness of the virtual wedge, are chosen such that a number of conditions are fulfilled. These conditions are related to the overall thickness variation between the thinnest and thickest part of the wedge and the thickness gradient of the wedge.

The overall thickness variation is chosen to have an overall energy variation of the beam when the beam is moved from the thinnest part of the wedge to the thickest part of the wedge. For example an overall energy variation that is larger than 5%. This means that a beam of a given energy that passes at the location of the thinnest part of the wedge or a beam that passes at the location of the thickest part of the wedge, has a difference in remaining energy of the beam after the wedge that varies by more than 5%. Typically, the overall thickness variation of the virtual wedge is chosen to correspond to the width of the Bragg peak in the target. So the overall thickness variation for the wedge can be determined by a classical planning device as corresponding to the water equivalent thickness variation between consecutive layers of a classical plan.

The thickness gradient defines how much the remaining energy of the beam after the wedge varies when varying the position of the beam on the wedge. For example, a variation of 0.5% in energy for a position variation of 1 cm on the wedge.

The material to be considered for the wedge can be for example water or a plastic material.

Hereafter, an irradiation plan is calculated using the standard known planning algorithms but based on the image that comprises both the target and the virtual wedge. With standard algorithms is understood the currently known algorithms for performing a treatment plan which are dividing the target volume in mono-energetic layers. The intermediated output of the planning device is a standard plan comprising a numbers of energy layers to be irradiated and for each energy layer, a number of spots with an associated dose and beam position are defined. Thereafter, to each spot, an intermediate particle beam energy is associated. The intermediate particle beam energy of a spot is corresponding to the energy of the layer the spot belongs to.

In a second step, the intermediate plan is transformed in a final plan suitable for irradiating the target without the physical presence of the wedge shaped element. For each spot, the intermediate particle beam energy, obtained for the intermediate plan, is adjusted by the planning device. For each spot, the algorithm of the planning device is configured to subtract from the intermediate particle beam energy, the energy loss of the particle beam through the virtual wedge. This energy loss depends on the position of the beam on the virtual wedge and on the material considered for the virtual wedge.

Hereafter, after the energy adjustment, the algorithm of the planning device is organizing all spots, in one or more sequences of spots. Preferably, the organization of the spots is such that the energy E(i) of the spots in each of the sequences is an increasing or decreasing monotonic function. As a consequence of the definition of the virtual wedge, the energy variation between consecutive spots will be defined by the thickness gradient of the wedge discussed above.

As shown in the lower part of FIG. 6, during irradiation of the target 140, no virtual wedge is used but a particle beam 150' is used, having an energy that is different from the beam 150 of the planning phase.

Second Example Algorithm of Planning Device:

In a second example of a planning device, no virtual wedge is used. In a first step, a standard treatment plan is calculated using a classical planning device which results in a number of layers having a number of spots. A schematic representation of an example of a number of layers and spots resulting from such an intermediate plan are shown in FIG. 7. Three layers L1, L2 and L3 are shown, each layer comprising a number of spots with corresponding energies E1, E2, E3. For example, layer L1 comprises six spots 10,11,12,13,14,15 having the same energy E1. In a second step, an iteration will be performed to alter the plan by imposing a number of parameter constraints. In this second step, the layers are renamed to sequences, in this example sequences S1, S2 and S3 are shown on FIG. 8.

In the second step, the constraint is imposed to maintain the variation of beam spot energy between two consecutive spots below a given maximum value. The given maximum value can be for example 5%, or more preferably 2%.

Therefore, starting from the intermediate plan, the energies of the spots within the sequences of the intermediate plan are adjusted to form a sequence of spots wherein the spot energy E(i) is an increasing or decreasing monotonic function. In the example in FIG. 8, the energy of sequence S1 is varied from Emax_S1 to Emin_S1. As shown in FIG. 8, the energies of the first spot 10 and the last spot 15 of the sequences are chosen such that the energy of the last point of a sequence is smaller than the energy of the first point of the next sequence. To determine the energies in a sequence, an extrapolation is for example made between energies of two subsequent layers defined in the intermediate plan. The order of the spots in the first sequence of the plan represented in FIG. 8 is: spot 10, spot 11, spot 12, spot 13, spot 14, spot 15.

Third Example Algorithm of Planning Device:

With a third example of an algorithm according to the invention, again as an intermediate step a standard planning is performed providing an intermediate output of layers having spots of the same energy. As an illustration consider the first layer of FIG. 7 having 6 spots 10,11,12,13,14,15 of the same energy E1. In a second step for a given spot of the intermediate plan, the algorithm is calculating a sequence of new energies and associates those energies to a new number of spots having the same (X,Y) coordinates. The dose D(i) defined by the intermediate plan is divided over the new number of spots defined. The dose of the spot of the intermediate plan can for example be divided equally over the new number of spots. This is illustrated in FIG. 9 where the intermediate spot 10 of the intermediate plan is split into five new spots 10e,10d,10c,10b,10a and those five spots have an energy between a maximum of E1 and the energy E2, the energy E2 being the energy of the next layer as defined in the intermediate plan. For a second spot 11 of the intermediate plan, a second sequence of spot energies going from E2 to E3 is defined. This is done for all spots of each layer of the intermediate plan. In FIG. 9 only one sequence S1 is shown corresponding to the intermediate layer L1 of FIG. 7. The sequence of spots of this sequence S1 is: spot 10a, spot 10b, spot 10c, spot 10d, spot 10e, spot 11a, spot 11b, spot 11c, spot 11d, spot 11e, spot 12a, ... until spot 15d. The advantage of this method is that more spots are defined compared to a standard planning and hence the overall energy change is spread out over more spots resulting in smaller energy variations and hence faster irradiation times.

Fourth Example Algorithm of Planning Device:

In a fourth example a treatment plan is considered wherein the energies of the spots are defined as part of an optimization process for reducing the irradiation time by taking into account the duration to vary parameter settings of the beam delivery system when an energy of the beam is to be changed.

Such a treatment plan comprises a number of parameters or functions related to the speed to vary a number of parameter settings of the beam delivery system. Parameters are for example the speed to vary the output energy of beam generator, the speed to vary a magnetic field in an electromagnet of the beam transport system or a speed to vary a scanning magnet. The speed to vary these parameter settings depends on the amount of energy variation of the beam. Hence, those parameters can for example be expressed as a function or a curve expressing a duration as function of a percentage of change of a given parameter setting.

In addition, in a preferred embodiment, such treatment plan comprises also a number of parameters that define a maximum allowable variation of beam energy from spot to spot. The total time it takes for the beam delivery system to deliver a sequence of spots will depend on various factors.

If we consider a first spot SP0 (E0, X0, Y0) and a second spot SP1 (E1, X1, Y1), then the following durations can be identified:

te1gen=the time to change the output energy of the beam generator from energy E0 to E1 te1BT=the time to change the magnetic field of the one or more electromagnets of the beam transport system corresponding to the energy change from E0 to E1, tx1=the time to change deflection of the beam in X from position X0 to position X1 ty1=the time to change deflection of the beam in Y from position Y0 to position Y1

As mentioned above those durations related to parameter settings are comprised in the planning device and can be stored in a data base.

When considering a control system according to the invention, as defined above, wherein the output energy of the generator, the magnetic field of the electromagnets of the beam transport system and the magnetic field of the scanning magnets are varied in parallel, the minimum time to change the settings of the beam delivery system to move from one spot to another spot having a different energy, is a value that can be determined.

Indeed, the minimum time Tm1 to move from spot SP0 to spot SP1 is then defined as the maximum duration of the above defined durations:

$$Tm1 = \text{Max}(te1gen, te1BT, tx1, ty1) \quad (1)$$

To determine a total irradiation time, one needs besides these durations (te1gen, te1BT, tx1, ty1) which are durations related to changes of parameter settings of the particle beam delivery system, also take into account the time Tdi required to deliver a prescribed dose D(i) to a spot i. This time to deliver a dose depends on the amount of planned dose D(i) to deliver and depends on the dose rate that the beam delivery system can perform. The dose rate depends on the beam current delivered by the beam delivery system. In this first example, we consider that the beam current is not varied from spot to spot or in other words that the dose rate is constant. The dose delivery time is the planned dose divided by the dose rate performed by the beam delivery system.

If we consider a full sequence of N spots, the total delivery time Ttot will be the sum of the time required to deliver the dose to each spot Tdk and of the time required to move from one spot to another Tmk.

$$Ttot = \Sigma_{k=1}^{n} Tm_k + \Sigma_{k=0}^{n} Td_k \quad (2)$$

In this example, the irradiation planning device according to the invention will minimize the time to move from one spot to another by optimizing the characteristics of the spots in the sequence, i.e. by optimizing the energy of the spots and by optimizing the positions of the spots. Indeed, as the time to vary the output energy and the magnetic field of the electromagnets depend on the amount of energy change, by keeping the energy variations from spot to spot small and by ordering the spots in an increasing or decreasing monotonic function, the beam delivery system will be able to perform faster irradiations.

This optimization of the irradiation time needs to occur in parallel or in sequence with the optimization targeting the clinical constraints of the treatment plan. Clinical constraints can be related to for example areas in which a dose and dose homogeneity is to be obtained or areas to where healthy tissue is to be spared. The optimization algorithm to be used is very similar to known existing iterative algorithms optimizing the plan according to the clinical constraints, except that an additional constraint related to the irradiation time is imposed.

In an alternative case, where also the dose rate needs to be adjusted from spot to spot, then the beam current also needs to be adjusted from spot to spot which results in an additional delay related to a parameter setting. In that case, an additional duration to vary for example the settings of the ion source from spot to spot needs to be taken into account. More in general, one can name tD1 the duration to vary a dose rate.

In this alternative case, the minimum time Tm1 to move from spot SP0 to spot SP1 is then defined as the maximum duration of the above defined durations:

$$Tm1 = \text{Max}(te1gen, te1BT, tx1, ty1, tD1) \quad (3)$$

And the total delivery time for all spots of a sequence is the same as defined above using equation (2).

Preferably, the irradiation planning device according to the invention will avoid large changes of energy which result in large delays for setting the particle delivery system parameter (which is of the order of one second). The irradiation planning device will consider only small delta changes of energy between 2 spots of the sequence.

With this optimization of the spots over the entire target volume, a target volume can be irradiated in just a few seconds.

According to a second aspect of the invention, the invention is also related to a method for irradiating a target or a phantom with a particle beam scanning technique. This method comprises the steps of
preparing an irradiation plan comprising steps of
 a) defining a number of spots wherein each spot has an associated beam position,
 b) associating a dose D(i) or a parameter proportional with a dose to each spot,
 c) associating an particle beam energy E(i) to each spot,
 d) organizing the spots in one or more sequences of spots according to the beam energy associated to each spot,
providing a particle beam generator configured for generating a particle beam and operable to vary an output energy,
providing a beam transport system for transporting the particle beam from the particle beam generator to a treatment location, the beam transport system comprising one or more electromagnets,
providing a scanning device located downstream of the beam transport system and comprising one or more scanning magnets configured for varying the position of the particle beam over the target,
irradiating the target following the order of the spots in the sequence of the one or more sequences of spots and use a control system configured for controlling in parallel
 a) a variation of an output energy of the particle beam generator, wherein the variation of the output energy corresponds to a variation of the spot energy between two consecutive spots from E(i) to E(j),
 b) a variation of a magnetic field of said one or more electromagnets of the beam transport system, wherein the variation of the magnetic field corresponds to the variation of the beam spot energy between two consecutive spots from E(i) to E(j),
 c) a variation of a magnetic field of the one or more scanning magnets of the scanning device, wherein the variation of the magnetic field corresponds to the variation of the beam spot energy between two consecutive spots from E(i) to E(j) and/or to a variation of the spot position between the two consecutive spots.

A phantom can for example comprise a water tank or a phantom made out of plastic or any other material.

Preferably, with the method according to the invention, the irradiation plan is prepared such that for each sequence of the one or more sequences of spots, the spot energy E(i) is an increasing or decreasing monotonic function.

More preferably, with the method according to the invention, the step of preparing an irradiation plan comprises a step of maintaining, for each sequence of said one or more sequences of spots, the variation of beam spot energy between two consecutive spots below a given maximum value.

According to the method of invention, the given maximum value is preferably equal to or smaller than 5%.

The present invention has been described in terms of specific embodiments, which are illustrative of the invention and not to be construed as limiting. More generally, it will be appreciated by persons skilled in the art that the present invention is not limited by what has been particularly shown and/or described hereinabove. The invention resides in each and every novel characteristic feature and each and every combination of characteristic features.

Reference numerals in the claims do not limit their protective scope. Use of the verbs "to comprise", "to include", "to be composed of", or any other variant, as well as their respective conjugations, does not exclude the presence of elements other than those stated. Use of the article "a", "an" or "the" preceding an element does not exclude the presence of a plurality of such elements.

The invention claimed is:

1. A particle therapy system for irradiating a target with a scanning beam technique, comprising:
 an irradiation planning device adapted to generate an irradiation plan for irradiating said target with said scanning technique, said plan comprising a number of spots, wherein each spot has an associated beam position, and wherein each spot has an associated dose or a parameter related to a dose;
 a particle beam generator adapted to generate a particle beam and to vary an output energy;
 a beam transport system adapted to transport the particle beam from the particle beam generator to a treatment location, said beam transport system comprising one or more electromagnets;
 a scanning device comprising one or more scanning magnets configured for varying the position of the particle beam over the target; and
 a control system adapted to receive the irradiation plan from the planning device and to deliver and control the irradiation of the target according to the irradiation plan,
  wherein at least one of said irradiation planning device or said control system comprises a planning algorithm adapted to associate a particle beam energy with each spot of the irradiation plan and to organize the spots in one or more sequences of spots according to the associated particle beam energy, and
  said control system is adapted to irradiate the target following the order of the spots in said one or more sequences of spots, and said control system comprises a process control device adapted to control, in parallel,
   a variation of an output energy of the particle beam generator, wherein the variation of the output energy corresponds to a variation of the spot energy between two consecutive spots
   a variation of a magnetic field of said one or more electromagnets of the beam transport system, wherein the variation of the magnetic field corresponds to said variation of the beam spot energy between two consecutive spots, and
   a variation of a magnetic field of the one or more scanning magnets of the scanning device, wherein the variation of the magnetic field corresponds to at least one of said variation of the beam spot energy between two consecutive spots or to a variation of the beam position between said two consecutive spots.

2. The system according to claim 1, wherein said planning algorithm is further adapted to organize the spots in each sequence of said one or more sequences of spots, such that the particle beam energy for consecutive spots is an increasing or decreasing monotonic function.

3. The system according to claim 1, wherein said control system is further adapted to interrupt the irradiation of the target during said parallel control of said variation of the output energy, said variation of the magnetic field of the one or more electromagnets and said variation of the magnetic field of the one or more scanning magnets.

4. The system according to claim 1, wherein said particle beam generator is further adapted to vary an intensity of the particle beam, and wherein said process control device is further adapted to control a variation of an intensity of the particle beam in parallel with said variation of the output energy, said variation of the magnetic field of the one or more electromagnets and said variation of the magnetic field of the one or more scanning magnets.

5. The system according to claim 1, wherein said beam transport system comprises a gantry device, and wherein said one or more electromagnets are installed in said gantry device.

6. The system according to claim 5, wherein said process control device is further adapted to control in parallel a variation of said output energy of the particle beam generator and a variation of a rotation angle of said gantry.

7. The system according to claim 1, further comprising:
a patient positioning device,
wherein said process control device is adapted to control in parallel a variation of said output energy of the particle beam generator and a variation of a position of said patient positioning device.

8. The system according to claim 1, wherein at least one of said one or more electromagnets of said beam transport system is a superconducting magnet.

9. The system according to claim 1, wherein said planning algorithm is further adapted to associate the particle beam energy to the spots such that the variation of the particle beam energy between two consecutive spots of said one or more sequences of spots remains below a predetermined maximum value.

10. The system according to claim 9, wherein said predetermined maximum value is related to at least one of a maximum speed to vary the output energy of the particle beam generator or a maximum speed to vary a magnetic field of said one or more electromagnets in the beam transport system.

11. The system according to claim 9, wherein said predetermined maximum value is equal to or smaller than 5%.

12. The system according to claim 1, wherein the beam position associated to each spot is defined with two parameters, wherein the parameters correspond to coordinates of a position of the particle beam in a plane perpendicular to an un-scanned beam direction.

13. The system according to claim 1, wherein at least one of said one or more sequences of spots comprises two consecutive spots having the same particle beam energy.

14. The system according to claim 1, wherein said planning algorithm is further adapted to define an intermediate plan, wherein the intermediate plan is adapted to account for the presence of a wedge shaped element located upstream of the target, and wherein said planning algorithm is further adapted to define a final plan, wherein the final plan is adapted to irradiate the target without said wedge by adjusting the particle beam energy of the spots of the intermediate plan and accounting for geometrical characteristics of the wedge shaped element.

15. A method for irradiating a target or a phantom with a particle beam scanning technique, comprising:
preparing an irradiation plan, wherein the preparing comprises:
defining a number of spots, wherein each spot has an associated beam position,
associating to each spot at least one of a dose or a parameter related to a dose,
associating a particle beam energy to each spot, and
organizing the spots in one or more sequences of spots according to the beam energy associated to each spot;
generating a particle beam, wherein the particle beam is adapted to have a variable output energy;
transporting the particle beam to a treatment location, using one or more electromagnets;
varying the position of the particle beam over the target using one or more scanning magnets; and
irradiating the target following the order of the spots in said sequence of said one or more sequences of spots and using a control system adapted to control, in parallel,
a variation of the output energy, wherein the variation of the output energy corresponds to a variation of the spot energy between two consecutive spots,
a variation of a magnetic field of said one or more electromagnets, wherein the variation of the magnetic field corresponds to said variation of the beam spot energy between two consecutive spots, and
a variation of a magnetic field of the one or more scanning magnets, wherein the variation of the magnetic field corresponds to at least one of said variation of the beam spot energy between two consecutive spots or to a variation of the beam position between said two consecutive spots.

16. The method according to claim 15, wherein preparing an irradiation plan further comprises organizing the spots in one or more sequences of spots such that for each sequence of said one or more sequences of spots, the spot energy is an increasing or decreasing monotonic function.

* * * * *

UNITED STATES PATENT AND TRADEMARK OFFICE
CERTIFICATE OF CORRECTION

PATENT NO. : 10,016,623 B2
APPLICATION NO. : 15/375259
DATED : July 10, 2018
INVENTOR(S) : Yves Claereboudt et al.

It is certified that error appears in the above-identified patent and that said Letters Patent is hereby corrected as shown below:

In the Claims

Claim 1, Column 16, Line 58, insert a --,-- after "two consecutive spots".

Signed and Sealed this
Seventh Day of May, 2019

Andrei Iancu
*Director of the United States Patent and Trademark Office*